US005475167A

United States Patent [19]

Nappa et al.

[11] Patent Number: 5,475,167

[45] Date of Patent: Dec. 12, 1995

[54] PROCESS FOR THE MANUFACTURE OF PENTAFLUOROETHANE

[75] Inventors: Mario J. Nappa, Newark; V. N. Mallikarjuna Rao; William R. Williams, both of Wilmington, all of Del.

[73] Assignee: E. I. Du Pont de Nemours and Company, Wilmington, Del.

[21] Appl. No.: 390,599

[22] Filed: Feb. 17, 1995

[51] Int. Cl.[6] .................................................... C07C 17/08

[52] U.S. Cl. .......................... 570/169; 570/164; 570/166; 570/168

[58] Field of Search .................................... 570/168, 169, 570/164, 166

[56] References Cited

U.S. PATENT DOCUMENTS

| | | | |
|---|---|---|---|
| 3,258,500 | 6/1966 | Swamer et al. | 260/653.7 |
| 3,755,477 | 8/1973 | Firth et al. | 260/653.4 |
| 4,828,818 | 5/1989 | Carlson et al. | 423/67 |
| 4,843,181 | 6/1989 | Gumprecht et al. | 570/169 |
| 5,036,036 | 7/1991 | Lerou | 502/317 |
| 5,334,787 | 8/1994 | Felix et al. | 570/169 |
| 5,354,928 | 10/1994 | Cheminal et al. | 570/169 |
| 5,399,549 | 3/1995 | Felix et al. | 570/169 |

FOREIGN PATENT DOCUMENTS

| | | | |
|---|---|---|---|
| 849024 | 8/1970 | Canada | 260/660 |
| 1196345 | 11/1985 | Canada | C07C 19/00 |
| 0514932 | 11/1992 | European Pat. Off. | C07C 19/08 |
| 0513823 | 11/1992 | European Pat. Off. | 570/169 |
| 19576 | 11/1992 | WIPO | 570/169 |

*Primary Examiner*—Werren B. Lone

[57] ABSTRACT

A process is disclosed for the preparation of pentafluoroethane from chlorotetrafluoroethane (the yield of pentafluoroethane is at least 50 mole percent based upon the amount of chlorofluoroethane reacted with HF) with particularly low levels of chlorofluoroethanes. The process involves providing sufficient pretreatment (where necessary) of a $Cr_2O_3$ catalyst with at least one agent selected from the group consisting of CO, $H_2$, $H_2O$ and mixtures thereof in the gaseous state such that the total chlorofluoroethane content of said product stream is less than 1 mole percent. Certain high surface area catalysts may be used without such pretreatment.

10 Claims, No Drawings

PROCESS FOR THE MANUFACTURE OF PENTAFLUOROETHANE

FIELD OF THE INVENTION

This invention relates to processes for the manufacture of halogenated ethanes, and more particularly to processes for the manufacture of pentafluoroethane by the catalytic hydrofluorination of halogenated ethanes.

BACKGROUND

It is known that $CHCl_2CF_3$ and $CHClFCF_3$ are obtainable in good yields from tetrachloroethylene, a readily available and relatively inexpensive commodity. However, the use of $CHCl_2CF_3$ and $CHClFCF_3$ as starting materials for the production of highly fluorinated hydrogen-containing products (such as pentafluoroethane) by reaction with HF has typically yielded appreciable amounts of perhalo by-products containing chlorine (evidently via side reactions). Undesirable chlorofluoroethanes have been especially noted when attempting to increase conversion to pentafluoroethane by operating at high temperatures. Chloropentafluoroethane (i.e., $CClF_2CF_3$ or CFC-115) is an especially deleterious by-product. Not only does it constitute a yield loss of the hydrogen-containing compounds, but it has a boiling point close to that of pentafluoroethane (i.e., $CHF_2CF_3$ or HFC-125) with the resulting mix being costly to separate.

U.S. Pat. No. 5,334,787 discloses a process for the preparation of $CHF_2CF_3$ by the reaction of a material selected from the group consisting of $C_2HCl_2F_3$ and $C_2HClF_4$ with HF, in the vapor phase, and in the presence of a solid $Cr_2O_3$ catalyst. Conditions are controlled whereby the formation of CFC-115 and other perhalo derivatives is minimized, and the examples illustrate obtaining $CF_3CHCl_2$ hydrofluorination products containing 1% or less, for each of $CF_3CH_2F$, $CClF_2CHF_2$, $CF_3CH_2Cl$, $CF_3CCl_2F$, $CClF_2CClF_2$, $CF_3CClF_2$, $CF_3CCl_3$, $CClF_2CCl_2F$ and $CClF_2CHClF$ (not all of these by-products are reported for each example). While the process illustrated in this patent represents a useful way of obtaining low amounts of perhalogenated ethane by-products, even the low amounts illustrated cause difficulties in purification. Accordingly, there is still a desire for processes which can provide pentafluoroethane in high yield with even lower production of perhalogenated impurities (especially $C_2Cl_2F_4$ and $C_2ClF_5$).

Pentafluoroethane is useful as a blowing agent, propellant, refrigerant, fire extinguishing agent, sterilant carrier gas, or heavy gas for an aerodynamic wind tunnel. It is desirable for its zero ozone depletion potential.

SUMMARY OF THE INVENTION

This invention provides an especially advantageous process for the preparation of pentafluoroethane with particularly low levels of chlorofluoroethanes. The process for producing pentafluoroethane of this invention is characterized by contacting a feed mixture of (i) monohydrochlorofluoroethane feed comprising at least 80 mole percent chlorotetrafluoroethane and (ii) HF feed, wherein the mole ratio of HF to chlorotetrafluoroethane in the feed mixture is between about 1.5:1 and 10:1, in the vapor phase with a $Cr_2O_3$ catalyst at a temperature between about 250° C. and 400° C. and for a contact time effective to form a vapor phase product stream containing pentafluoroethane, wherein the yield of pentafluoroethane is at least 50 mole percent based upon the amount of chlorotetrafluoroethane reacted; and providing sufficient pretreatment (where necessary) of the $Cr_2O_3$ catalyst with at least one agent selected from the group consisting of CO, $H_2$, $H_2O$ and mixtures thereof in the gaseous state such that the total chlorofluoroethane content of said product stream is less than 1 mole percent. Preferably, the total $C_2ClF_5$ content of the product stream is less than 3000 ppm and the total $C_2Cl_2F_4$ content of the product stream is less than 2000 ppm.

DETAILED DISCUSSION

The present invention provides a process for the manufacture of pentafluoroethane by contacting a mixture of hydrogen fluoride and at least one compound selected from the group consisting of 1,1,1,2-tetrafluorochloroethane (i.e., $CHClFCF_3$ or HCFC-124) and 1,1,2,2-tetrafluorochloroethane (i.e., $CHF_2CClF_2$ or HCFC-124a) in the presence of selected chromium oxide catalysts. The starting compound(s) can be represented by the formula $C_2HClF_4$. The starting compound(s) can be $CHClFCF_3$, or can be $CHF_2CClF_2$, or can be a mixture of $CHClFCF_3$ and $CHF_2CClF_2$.

The catalysts used for the process of this invention are sufficiently pretreated to limit the formation of chlorofluoroethanes (i.e., perhalogenated ethanes containing both chlorine and fluorine) as indicated above. In the case of $Cr_2O_3$ having surface area greater than about 100 $m^2/g$, no pretreatment is generally necessary to provide a process where the formation of chlorofluorethanes is limited to 1 mole percent or less of the product stream; whereas $Cr_2O_3$ having a surface area of about 50 $m^2/g$ generally does require pretreatment to achieve this performance.

Preferred catalysts of this invention are sufficiently pretreated (where required) to achieve product streams where the total chlorofluoroethane content is 0.5 mole percent or less; and the most preferred catalysts of this invention are sufficiently pretreated (where required) to achieve a product stream where the total chlorofluoroethane content is 0.2 mole percent or less. Preferred catalysts include $Cr_2O_3$ prepared by pyrolysis of $(NH_4)_2Cr_2O_7$, and vapor-phase pretreatment of the resulting solid $Cr_2O_3$ with CO, $H_2$ and/or $H_2O$; and $Cr_2O_3$ having a surface area of about 200 $m^2/g$ or more.

The $Cr_2O_3$ catalyst prepared using the pyrolysis of ammonium dichromate, can be prepared by any method known to the art including those disclosed in U.S. Pat. Nos. 4,843,181 and 5,036,036, which are incorporated herein by reference. The $Cr_2O_3$ obtained in this manner may contain low levels of contaminants (e.g., potassium) which are present as a result of the manufacturing process for the original $(NH_4)_2Cr_2O_7$. The level of potassium or other water-soluble impurities may be reduced by water-washing in a conventional manner.

Other $Cr_2O_3$ catalysts which may be used in the process of this invention include catalysts having a surface area as determined by BET measurement greater than about 100 $m^2/g$, some of which are commercially available. The preparation of such high surface area $Cr_2O_3$ catalysts is described in U.S. Pat. No. 4,828,818 and in European Patent Application Publication No. 514,932.

The form of the catalyst is not critical and may be used as pellets, powders or granules.

Where pretreatment with vapor-phase CO, $H_2$, and/or $H_2O$ is used, the chromium oxide is normally dried in a stream of nitrogen before the pretreatment. Without confining the invention to any particular theory of operation, it is thought that this pretreatment reduces the type of active sites responsible for the formation of perhalogenated ethanes. Typically, the pretreatment involves heating the catalyst with the above vapors at an elevated temperature (typically from 100° C. to 400° C.) for about an hour. Higher or lower pretreatment temperatures may be used by adjusting the pretreatment times accordingly. Where pretreatment with CO, $H_2$ and/or $H_2O$ is used, it is preferably sufficient to reduce the CFC-115 content of the product stream by at least 20% compared to untreated $Cr_2O_3$ catalyst; and is more preferably sufficient to reduce the CFC-115 content by at least 40% compared to untreated $Cr_2O_3$ catalyst.

Typically, the pretreated $Cr_2O_3$ will be treated with a vapor phase fluorination agent such as $CCl_3F$ or HF prior to use for pentafluoroethane production. This treatment can be accomplished by placing the $Cr_2O_3$ (whether or not pretreated with vapor-phase CO, $H_2$ and/or $H_2O$) in a suitable container (which can be the reactor to be used to perform the hydrofluorination of the instant invention) and thereafter passing HF over the dry $Cr_2O_3$ for a suitable period of time (e.g., about 15 to 300 minutes) at a suitable temperature (e.g., about 200° C. to 450° C.).

The contacting of the chlorotetrafluoroethane and HF with the catalyst of the instant invention is performed at effective temperature, mole ratio and contact time. By effective temperature, mole ratio and contact time is meant the temperatures, mole ratios and contact times which produce a product stream which contains $CHF_2CF_3$ in a major proportion, (i.e., in an amount of at least about 50 mole percent based upon $C_2HClF_4$ reacted). Preferably these factors are controlled to provide a product stream which contains at least about 60 mole percent $CHF_2CF_3$ based upon the $C_2HClF_4$ reacted.

Suitable reaction temperatures are normally within the range of from about 250° C. to about 400° C. Preferred temperatures range from about 350° C. to 390° C. Of note are embodiments where the reaction temperature is about 375° C., and above. The mole ratio of HF to $C_2HClF_4$ fed to the reaction will normally be within the range from about 1.5:1 to about 10:1, and is preferably from about 1.5:1 to 4:1 (e.g., 2:1). The term contact time as used herein is the bulk volume of the catalyst divided by the total volumetric vapor-phase feed rate. The contact time can vary widely, but will generally be in the range of from about 1 to 100 seconds, preferably 4 to 10 seconds. Of note are embodiments where the contact time is 9 seconds or less. The reaction pressure is not critical but should be sufficient to maintain HF, the organic reactant and the reaction product stream components in the vapor state at the operating temperature.

In general, the higher the temperature, the greater the HF to monohydrochlorofluoroethane reactant mole ratio, and the longer the contact time, the greater is the conversion of the reactants to fluorinated products, and the greater is the degree of fluorination of the raw material. The above variables can be balanced, one against the other, so that formation of $CHF_2CF_3$ is maximized and that of perhalogenated by-products is minimized, preferably with that of $CClF_2CF_3$ and $C_2Cl_2F_4$ to less than 0.5 mole percent each, more preferably to less than 0.3 mole percent $CClF_2CF_3$, and less than 0.2 mole percent total $C_2Cl_2F_4$ (i.e., total $CCl_2FCF_3$ plus $CClF_2CClF_2$).

In some cases, the $C_2HClF_4$ feed will contain minor amounts of one or more of the less fluorinated monohydrochlorofluoroethanes such as $C_2HCl_2F_3$; and/or the product stream from the reaction may include one or more of such compounds. For continuous processes, unreacted starting material and monohydrochlorofluoroethanes which are less fluorinated than chlorotetrafluoroethane can be recycled to the reactor for the production of additional $CHF_2CF_3$. Accordingly, a portion of the feed mixture which is fed to the reaction zone can comprise at least one compound selected from the group consisting of $C_2HCl_3F_2$ and $C_2HCl_2F_3$, fresh and/or obtained as recycle. However, the monohydrochlorofluoroethane component fed to the reaction zone should contain at least about 80 mole percent $C_2HClF_4$.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel. Silicon carbide is also suitable for reactor fabrication. The process of this invention can be carried out readily in the vapor phase using well known chemical engineering practice.

Practice of the invention will become further apparent from the following non-limiting examples.

EXAMPLES

General Catalyst Activation Procedure

A ⅜" (9.5 mm) I.D.×15" (381 mm) Hastelloy® C nickel alloy reactor was charged with a $Cr_2O_3$ catalyst, 20 g when $Cr_2O_3$ prepared by the pyrolysis of $(NH_4)_2Cr_2O_7$ (Catalyst A) was used or 18.5 g when high surface area (above 200 $m^2/g$) chrome oxide (Catalyst B) was used. The catalyst was pretreated as described in Examples 1 to 5. The pretreated catalyst was then heated to 175° C. in a flow of nitrogen and hydrogen fluoride, 25 cc/min of each, for about one hour. The temperature was then increased at the rate of 50° C. every 0.5 hour to a final temperature of 400° C. At 350° C., the nitrogen flow was reduced to 20 cc/min and the HF flow increased to 80 cc/min. The reactor temperature was maintained at 400° C. for one hour. The reactor was then brought back to the desired operating temperature, the nitrogen flow stopped, and the flow of reactants started.

General Catalyst Testing Procedure

A 2:1 molar ratio mixture of hydrogen fluoride and $CHClFCF_3$ (HCFC-124) was passed over the catalyst. The HCFC-124 flow rate was 20 g/hr. The reaction temperature was varied from 275° C. to 400° C. The experimental results which afforded 67% HFC-125 yield are shown in Table 1.

General Analytical Procedure

The reactor effluent was sampled on-line with a Hewlett Packard HP 5890 gas chromatograph using a 20 foot (6.1 m) long, one-eighth inch (0.32 cm) diameter, column containing Krytox® perfluorinated polyether on an inert support and a helium flow of 35 cc/min. Gas chromatographic conditions were 60° C. for three minutes followed by temperature programming to 180° C. at a rate of 8° C./minute. The table percentages are in mole %.

Example 1

Hydrogen Pretreatment

The reactor was charged with Catalyst A, dried in a stream of nitrogen at 400° C. for about 8 hours, and then cooled to 175° C. The catalyst was then treated with hydrogen (50 cc/min) for one hour at 175° C. The hydrogen flow was stopped and the catalyst activated according to the General Catalyst Activation Procedure. The catalyst was then tested using the General Catalyst Testing Procedure. The results are shown in Table 1.

Example 2

Water Vapor Pretreatment

The reactor was charged with Catalyst A, dried in a stream of nitrogen at 400° C. for about 8 hours, and then cooled to 175° C. The catalyst was then treated for one hour at 175° C. with nitrogen (50 cc/min) which had been bubbled through room temperature water. The flow was stopped and the catalyst activated according to the General Catalyst Activation Procedure. The catalyst was then tested using the General Catalyst Testing Procedure. The results are shown in Table 1.

Example 3

Water Vapor and Hydrogen Pretreatment

The reactor was charged with Catalyst A, dried in a stream of nitrogen at 400° C. for about 8 hours, and then cooled to 175° C. The catalyst was then treated for one hour at 175° C. with nitrogen (50 cc/min) which had been bubbled through room temperature water. The flow was stopped and the temperature was increased to 400° C. and maintained for eight hours. The reactor was cooled to 175° C. and the catalyst was then treated with hydrogen (50 cc/min) for one hour at 175° C. The hydrogen flow was stopped and the temperature was increased to 400° C. and maintained for eight hours. The catalyst was activated according to the General Catalyst Activation Procedure. The catalyst was then tested using the General Catalyst Testing Procedure. The results are shown in Table 1.

Example 4

Carbon Monoxide Pretreatment

The reactor was charged with Catalyst A and purged with nitrogen. The catalyst was then heated in a stream of carbon monoxide (100 cc/min) to 400° C. and the temperature maintained under CO flow for about 8 hours. The catalyst was slowly cooled under a nitrogen purge followed by activation according to the General Catalyst Activation Procedure. The catalyst was then tested using the General Catalyst Testing Procedure. The results are shown in Table 1.

Example 5

Carbon Monoxide and Water Vapor Pretreatment

The reactor was charged with Catalyst A and purged with nitrogen. The catalyst was then heated in a stream of carbon monoxide (100 cc/min) to 400° C. and the temperature maintained under CO flow for about 8 hours. The catalyst was slowly cooled under a nitrogen purge. The catalyst was then treated for one hour at 175° C. with nitrogen (50 cc/min) which had been bubbled through room temperature water. The flow was stopped and the catalyst was heated under a nitrogen flow of 50 cc/min for eight hours at 400° C., followed by activation according to the General Catalyst Activation Procedure. The catalyst was then tested using the General Catalyst Testing Procedure. The results are shown in Table 1.

Example 6

High Surface Area Chromium Oxide

The reactor was charged with Catalyst B and nitrogen (100 cc/min) was passed over the catalyst while heating it to 400° C. This temperature was maintained for about 8 hours followed by cooling to 175° C. The nitrogen flow was stopped and the catalyst activated according to the General Catalyst Activation Procedure. The catalyst was then tested using the General Catalyst Testing Procedure. The results are shown in Table 1.

TABLE 1

| | | HF + 124 → 125 + HCl, conditions to form 67% 125 | | | | | | |
|---|---|---|---|---|---|---|---|---|
| Ex. | T (°C.) | HCFC-123[1] | HCFC-124[2] | HCFC-133a[3] | Total CFCs[4] | CFC-115[5] | Total $C_2F_4Cl_2$ | others[6] |
| STD[7] | 360 | 8.2% | 22.4% | 1.2% | 0.67% | 0.37% | 0.25% | 0.49% |
| 1 | 389 | 5.9% | 24.9% | 1.3% | 0.35% | 0.17% | 0.16% | 0.54% |
| 2 | 378 | 6.8% | 24.3% | 1.1% | 0.35% | 0.17% | 0.16% | 0.43% |
| 3 | 356 | 6.0% | 25.3% | 0.9% | 0.42% | 0.21% | 0.19% | 0.38% |
| 4 | 385 | 6.1% | 25.0% | 0.9% | 0.43% | 0.23% | 0.18% | 0.47% |
| 5 | 375 | 6.2% | 26.0% | 0.3% | 0.35% | 0.18% | 0.15% | 0.14% |
| 6 | 369 | 6.4% | 25.9% | 0.4% | 0.18% | 0.06% | 0.10% | 0.20% |

1. 123 is $CHCl_2CF_3$
2. 124 is $CHClFCF_3$
3. 133a is $CH_2ClCF_3$
4. Total CFCs include $CClF_2CF_3$, $C_2Cl_2F_4$ (at least one isomer), and one or more of $C_2Cl_3F_3$ (both isomers) and $C_2FCl_3$.
5. 115 is $CClF_2CF_3$
6. Others include $CH_2FCF_3$, $CHClFCClF_2$, $CHF_2CClF_2$, $C_2Cl_4$, and $C_2HCl_3$.
7. STD is Catalyst A with only HF treatment. When this catalyst was tested with $CHCl_2CF_3$ as described in U.S. Pat. No. 5,334,787, the results were substantially the same as illustrated in that patent.

What is claimed is:

1. A process for producing pentafluoroethane, characterized by:

contacting a feed mixture of (i) monohydrochlorofluoroethane feed comprising at least 80 mole percent chlorotetrafluoroethane and (ii) HF feed, wherein the mole ratio of HF to chlorotetrafluoroethane in the feed mixture is between about 1.5:1 and 10:1, in the vapor phase with a $Cr_2O_3$ catalyst at a temperature between about 250° C. and 400° C. and for a contact time effective to form a vapor phase product stream containing pentafluoroethane, wherein the yield of pentafluoroethane is at least 50 mole percent based upon the amount of chlorotetrafluoroethane reacted; and providing sufficient pretreatment of the $Cr_2O_3$ catalyst with at least one agent selected from the group consisting of CO, $H_2$, $H_2O$ and mixtures thereof in the gaseous state such that the total chlorofluoroethane content of said product stream is less than 1 mole percent.

2. The process of claim 1 wherein the total $C_2ClF_5$ content of the product stream is less than 3000 ppm and the total $C_2Cl_2F_4$ content of the product stream is less than 2000 ppm.

3. The process of claim 1 wherein the $Cr_2O_3$ is prepared by pyrolysis of $(NH_4)_2Cr_2O_7$ and pretreatment with said at least one agent.

4. The process of claim 1 wherein the $Cr_2O_3$ has a surface area of about 100 $m^2/g$ or more.

5. The process of claim 1 wherein the $Cr_2O_3$ has a surface area of about 200 $m^2/g$ or more.

6. The process of claim 1 wherein the mole ratio of HF to $C_2HClF_4$ in the feed mixture is within the range of from about 1.5:1 to about 4:1.

7. The process of claim 1 wherein the reaction temperature is within the range of from about 350° C. to 390° C.

8. The process of claim 1 wherein the contact time is from about 4 to 9 seconds.

9. The process of claim 1 wherein the process is continuous; wherein unreacted starting material and monohydrochlorofluoroethanes which are less fluorinated than chlorotetrafluoroethane are recycled.

10. The process of claim 1 wherein the catalyst is pretreated with at least one agent selected from the group consisting of CO, $H_2$ and $H_2O$ in the gaseous state; and the pretreated catalyst is treated with a vapor phase fluorination agent prior to use for pentafluoroethane production.

* * * * *